United States Patent [19]

Mehl

[11] Patent Number: 4,774,058

[45] Date of Patent: Sep. 27, 1988

[54] APPARATUS FOR, AND METHODS OF, OPERATING UPON A FLUID

[76] Inventor: Ehrenfried L. Mehl, Kraepelinstr. 4a, 8 Munich 40, Fed. Rep. of Germany

[21] Appl. No.: 780,312

[22] Filed: Sep. 26, 1985

[51] Int. Cl.⁴ ............................................. B01D 13/00
[52] U.S. Cl. ................... 422/101; 210/266; 210/282; 210/317; 210/497.3; 210/323.1
[58] Field of Search ........... 210/266, 282, 317, 433.2, 210/497.3; 422/101

[56] References Cited

U.S. PATENT DOCUMENTS

| | | | |
|---|---|---|---|
| 345,318 | 7/1886 | Poor | 210/497.2 X |
| 768,605 | 8/1904 | Keller et al. | 422/101 |
| 793,475 | 6/1905 | Ulander | 210/497.3 X |
| 3,238,056 | 3/1966 | Pall et al. | 210/505 X |
| 3,625,652 | 12/1971 | Fujimoto et al. | 210/266 X |
| 4,142,858 | 3/1979 | Acuff | 422/101 |
| 4,246,339 | 1/1981 | Cole et al. | 422/101 |
| 4,272,481 | 6/1981 | Ahlstrom | 422/101 X |
| 4,357,240 | 11/1982 | Mehra et al. | 422/101 X |
| 4,427,415 | 1/1984 | Cleveland | 422/101 |
| 4,434,235 | 2/1984 | Rabi et al. | 422/101 |
| 4,483,925 | 11/1984 | Noack | 422/101 X |
| 4,526,690 | 7/1985 | Kiovsky et al. | 210/433.2 |

FOREIGN PATENT DOCUMENTS

WO82/03690 10/1982 PCT Int'l Appl. .

OTHER PUBLICATIONS

Millipore Catalogue and Purchasing Guide, 1978, Cat. No. MC 177/U, copyright 1977, Millipore Corp., Bedford, Mass., p. 31.

Primary Examiner—Frank Sever
Attorney, Agent, or Firm—Darby & Darby

[57] ABSTRACT

A filter comprises a nonporous support member open at one end and a porous disc rigidly secured to the support member at an opposite, preferably smaller, end. The disc may be formed from fibers preferably having a thickness of approximately 0.5–50 micrometers, or it may be formed from a plurality of particles or beads retained by a pair of membranes. When the disc is relatively small such as approximately 1 millimeter in diameter, it may be pressed into a constricted end of the support member. When the disc has an increased diameter, it may be rigidly supported by a retainer preferably made from a mesh material and welded to the support member. For even larger disc sizes, the disc may be supported between two (2) retainers preferably welded to the support member. A plurality of receptacles may be disposed in a tray to, serve as the filters, or receive the filters. The fluid may be introduced into, and retained in, the support members and discs by capillary action. The fluid may be passed through the filters by centrifuging the tray with the filters. The trays bearing the filters may be centered in a container to inhibit contact with the container walls and fluid vapor may be passed through the container to interact with material on the centered filters. An absorbent sheet moistened with the fluid may be positioned against the container walls to maximize vapor content within the container.

12 Claims, 2 Drawing Sheets

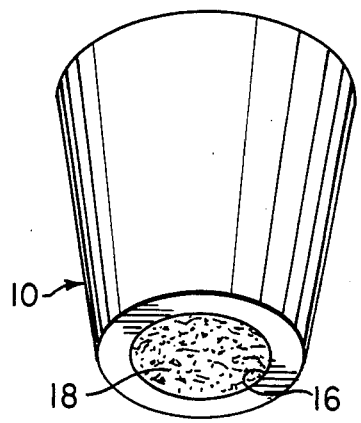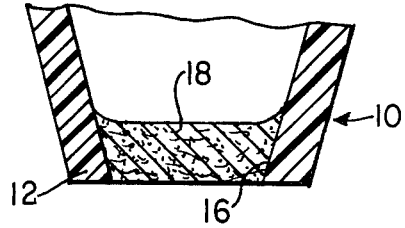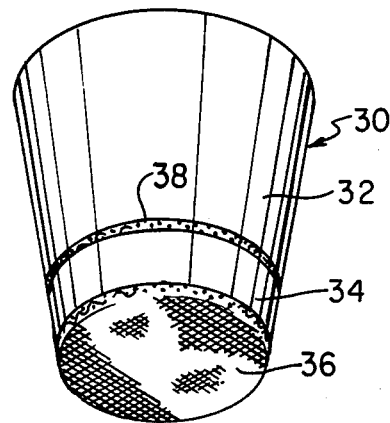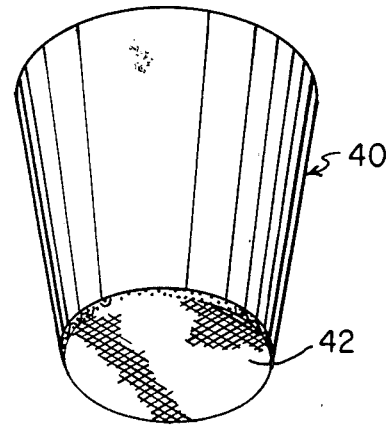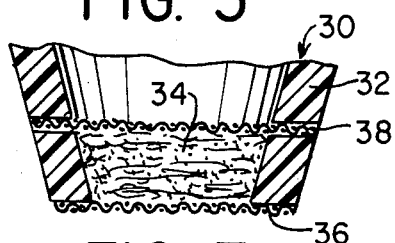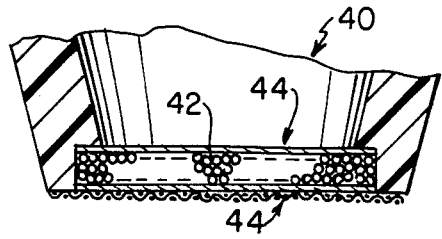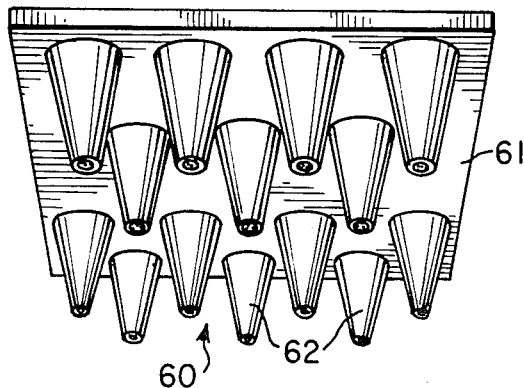

APPARATUS FOR, AND METHODS OF, OPERATING UPON A FLUID

This invention relates to methods of operating upon fluids to filter such fluids, to obtain affinity binding of the fluid components to other substances or obtain reactions of fluid components. The invention also relates to articles and apparatus for providing such operations on the fluids.

Fluids are introduced into filters for various purposes. For example, fluids may be introduced into filters to achieve absorption or adsorption of fluid components by materials in the filters. In another type of relationship, fluids may be introduced into filters to react chemically with other reagents in the filters. Still other fluids may be introduced into filters to ionize and become bound by ionic interaction with other ionized materials in the filters. In other types of relationships, fluids may be introduced into a filter and may become coupled to materials on or in the filter by other types of affinity than those specified above.

As will be appreciated, the introduction of fluids into filters for the purposes described in the previous paragraph occurs millions, and even billions, of times throughout the world in every year. In recent years, such introduction of fluids into filters has multiplied because of the considerable expansion of activity in the bio-engineering field. In spite of such extensive use and such expanded activities, some serious deficiencies exist in the methods of, and apparatus for, acting on fluids in filters. For example, the filters have dead spaces which inhibit a complete operation on the fluid in the filters and which prevent the filters from being cleansed after a given operation so that they can subsequently receive other fluids for further operations. The filters are also disadvantageous because they are relatively large and accordingly require large amounts of fluid to obtain a defined operation on such fluids. Other disadvantages are that the filters are not effective in facilitating the desired reactions on the fluids which they receive. The disadvantages discussed above have existed for many years in spite of extensive efforts to eliminate them.

This invention provides methods of, and articles and apparatus for minimizing or eliminating the disadvantages discussed in the previous paragraph. The articles of this invention include filters which provide no dead space so that a complete operation can be performed on all of the fluid introduced into the filters. Furthermore, the filters are constructed in such a manner as to insure that all of the fluid introduced into the filters is properly processed.

The filters of this invention are relatively small so that the amount of fluid introduced into the filters is minimized. However, the volume of the fluid being processed can be expanded to any desired level by disposing a plurality of filters in a tray. The filters of this invention are further advantageous in that they are disposable. This allows the filters to be used only for a single operation and then discarded. The disposability of the filters is enhanced because the filters can be manufactured inexpensively.

One embodiment of the invention provides a filter comprising a nonporous support member open at one end and a porous disc rigidly secured to the support member at an opposite, preferably smaller, end. The disc may be formed from fibers preferably having a thickness of approximately 0.5-50 micrometers, or it may be formed from a plurality of particles or beads retained by a pair of membranes. Because of ease of construction, this porous member is normally of discus shape and herein is designated as a disc. It should be recognized that the material constituting the porous member should be in close contact with the nonporous support, and thus its final shape will be determined by the construction of the nonporous member.

When the disc is relatively small, such as approximately 1 millimeter in diameter, it may be pressed into a constricted end of the support member. When the disc has an increased diameter, it may be rigidly supported by a layer preferably made from a mesh material and welded to the support member. For even larger disc sizes, the disc may be supported between two (2) layers preferably welded to the support member.

A plurality of receptacles may be disposed in a tray to serve as the filters, or receive the filters, in a relationship for providing for a flow of fluid through the filters. The fluid may be passed through the filters by centrifuging the trays bearing the support members.

The trays may be centered in a container to inhibit contact with the container walls and fluid vapor may be passed through the container to interact with material on the centered filters. An absorbent sheet moistened with said fluid may be positioned against the container walls to maximize vapor content within the container.

In the drawings:

FIG. 1 is a schematic perspective view of a filter constituting one embodiment of the invention;

FIG. 2 is an enlarged, fragmentary, schematic elevational view of a cross section of the filter shown in FIG. 1 and particularly illustrates the configuration of a disc when the disc is assembled in the filter;

FIG. 3 is an enlarged schematic elevational view of a cross section of the disc shown in FIG. 2 before the disc is assembled in the filter;

FIG. 4 is a schematic perspective view, similar to that shown in FIG. 1, of a filter constituting a second embodiment of the invention;

FIG. 5 is an enlarged, fragmentary, schematic view in elevation of a cross section of a disc assembly which is included in the embodiment of the filter shown in FIG. 4;

FIG. 6 is a schematic perspective view, similar to that shown in FIGS. 1 and 4, of a filter constituting a third embodiment of the invention;

FIG. 7 is an enlarged, fragmentary, schematic view in elevation of a cross section of a disc assembly which is inluded in the embodiment of the filter shown in FIG. 6;

FIG. 8 is a schematic perspective view of a tray containing receptacles for serving as filters, or for receiving filters, constructed as shown in the previous Figures;

Figure 9:
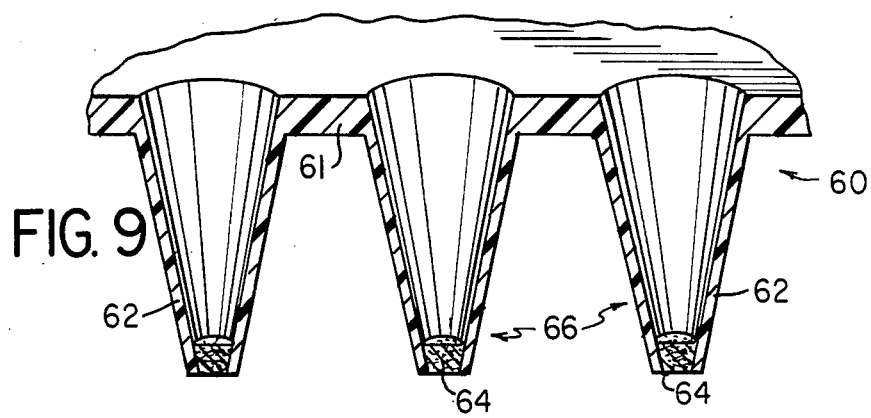
FIG. 9 is a fragmentary perspective view of a cross section of the tray shown in FIG. 8 and of the filters positioned in the tray.
Figure 10:
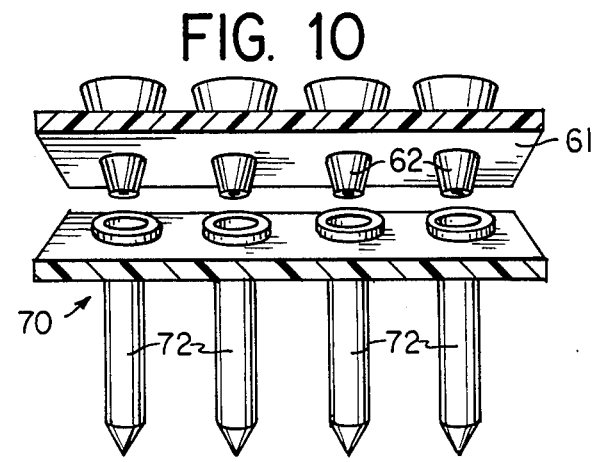
Figure 11:
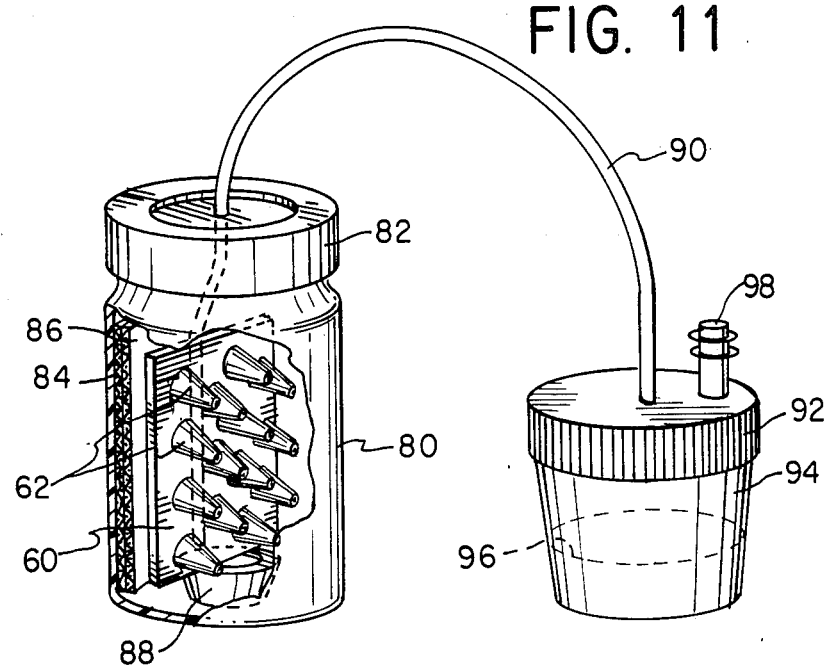

FIG. 10 is a schematic exploded perspective view of the filters disposed in the receptacles in a tray, the receptacles in the tray in turn being disposed for a cooperative relationship with receiving tubes in a holder so that the filters, the tray and the holder can be used in centrifugation, and FIG. 11 is a schematic perspective view of apparatus for introducing fluid reactants and/or solvents in vapor form onto the filters in the tray shown in FIGS. 8, 9 and 10.

In the embodiment of the invention shown in FIGS. 1, 2 and 3, a filter generally indicated at 10 is provided.

The filter includes a support member 12 made from a suitable nonporous material such as polypropylene or glass. The support member 12 may also be made from other suitable materials such as polyethylene, tetrafluorethylene (designated by E. I. DuPont de Nemours of Wilmington, Del., as "Teflon"), plastic-coated composite materials with a metal or silica base and perfluoroalkoxy derivatives.

The support member 12 has an open end 14 and an end 16 opposite the open end 14. Preferably the support member 12 has a form, such as a conical form, wherein the end 14 is larger than the end 16. The support member 12 may be commercially available. For example, suitable support members 12 can be cut from Eppendorf pipet tip designated as Part Number 5089-801 provided by American Scientific Product.

A filter disc 18 is inserted as by pressure into the end 16 of the support member 12. The disc 18 may be made from a suitably porous material having woven or nonwoven characteristics. Preferably the disc 12 is formed from suitable fibers such as glass, carbon, quartz or plastic materials such as an acrylic, polypropylene or a tetrafluoroethylene such as that designated by E.I. DuPont de Nemours by the trademark "Teflon". The disc 18 may also be made from any combination of materials such as those specified above. When the disc 18 is inserted into the end 16 of the support member 14, it is so rigidly held by the support member that it does not become dislocated even when the filter 10 is centrifuged at speeds as high as ten thousand revolutions per minute (10,000 rpm). Although the member 18 has been designated as a disc, it may be generically considered as a porous plug having any desired shape, but which will provide a precise uniform plane for contact with blotting paper. As used in the claims, the term "disc" is used in the generic sense.

Preferably the filter 10 has a small size. For example, the opening 16 in the support member 12 may have a diameter of approximately one millimeter (1 mm) and the filter disc 18 may have a diameter in the order of one and two tenths millimeters (1.2 mm). The thickness of the disc 18 may be in the order of four tenths millimeter (0.4 mm). The thickness of the fibers in the disc may be in the order of one half of a micrometer (0.5 $\mu$m) to fifty micrometers (50 $\mu$m). The length of the support member 12 may be in the order of six and one half millimeters (6.5 mm).

The filter 10 described above has certain important advantages. It is so small that it can receive fluid in the support member 12 as by capillary action. For example the filter 10 can be inverted and dipped into a receptacle (not shown) containing fluid. This fluid is then received in the support member 12 and is retained in the support member even while the support member is removed from the receptacle. The filter 10 can then be inverted to its upright form (shown in FIG. 1) while the fluid is retained in the support member 12.

Fluid can also be received in the support member 12 with the support member upright. This can be accomplished by dipping the plugged end 16 into the fluid in a receptacle (not shown). Fluid then flows through the disc 18 into the support member 12 as by capillary action. The fluid is then retained in the support member 12 as by capillary action. Fluid may also be transferred into the disc 18 by contacting the tip 16 to a wick-like material containing the fluid.

In addition to providing for the flow of fluid, and the retention of fluid, in the support member 12 as by capillary action, the filter 10 also has other important advantages. For example, it retains the disc 18 in a rigid relationship with the support member 12 only as a result of the pressure between the disc and the support member. In this rigid relationship, no fluid is able to leak through the filter 10 at the boundary between the support member 12 and the disc 18. This rigid and leakproof relationship is maintained even when the filter is centrifuged at forces as high as ten thousand times gravity (10,000 g).

The disc 18 may be either unmodified or modified such as by chemicals. Modification of filters as by chemicals is well known in the art. For example, the disc 18 may be derivatized as by trimethylsilylation to provide for a sequencing of amino acids from a peptide. Derivatizing filters is provided in a number of widely divergent applications which are well known in the art.

The filter 10 also has other important advantages. For example, the fluid in the support member 12 can be transferred from the support member as by blotting paper disposed against the disc 18. Furthermore, with the dimensions specified above, the disc 18 retains a volume of fluid of only approximately one half of a microliter (0.5 $\mu$l). This provides for an economic use of derivatized filter material in the disc 18 and results in nearly quantitative emptying of the fluid in the filter as by centrifuging. Furthermore, because of the small size of the disc 18, background effects in the disc are minimized, thereby enhancing the sensitivity of detecting substances in the low picomole or femtomole range.

The disc 10 may be individually cut from a strip of filter paper as by a cutting tooland may be retained in the cutting tool during transfer into the opening 16 in the support member 12. The cutting tool may be made from a stainless steel canula having an outer diameter of one and four tenths millimeter (1.4 mm), an inner diameter of one and two tenths millimeter (1.2 mm) and a length of fifty millimeter (50 mm). The cutting tool may be a stainless steel canula containing a slideable stainless steel rod for extrusion and positioning of the disc 18. The diameter of the rod may be one and one tenth millimeter (1.1 mm).

For finally positioning the disc 18 into the opening 16 in the support member 14, thesupport member 12 may be inverted and disposed on a platemade from a suitable material such as glass. The disc 18 may then be compressed as with the stainless steel rod until the disc is within the end of the support member 12. The compression of the disc 18 is sufficient to maintain it in place in the opening 14 without any need for any screens, seals or holders even at centrifugal forces as high as ten thousand times gravity (10,000 g).

FIGS. 4 and 5 illustrate another embodiment of a filter included within this invention. The filter shown in FIGS. 4 and 5 is generally larger in size than the filter 10 shown in FIGS. 1, 2 and 3. The filter shown in FIGS. 4 and 5 is generally indicated at 30 and is provided with a support member 32. The support member 32 may be made from the same material as the support member 12 and may be provided with the same relative configuration as the support member 12.

The filter 30 includes a disc 34 preferably made from substantially the same material as the disc 18. The disc 34 may be provided with a suitable diameter such as in the order of four millimeters (4 mm). The disc 34 may be rigidly supported within the member 32 as by at least one retainer 36. The retainer 36 may be provided with a mesh configuration and may be made from a suitable material such as a tetrafluoroethylnne (Teflon). The material constituting the support member 32 may be melted as by heat to achieve adherence onto the retainer 36 to provide a unitary relationship. However, the disc 34 may be further restricted by a second retainer 38 in a similar unitary relationship as in the retainer 36.

The retainers 36 and 38 may be provided with a suitable mesh such as in the order of four thousandths of an inch (0.004"). The fusing or welding may occur at a temperature of approximately 135° C. for a period of time such as approximately ten (10) seconds when the support member 32 is made from polypropylene.

FIGS. 6 and 7 illustrate a third embodiment of a filter constituting this invention. In this embodiment, a filter generally indicated at 40 is provided. The filter 40 may be constructed in a manner similar to that shown in FIGS. 4 and 5 and described above except for the construction of a disc 42 which is included in the filter. This disc may be formed from a pair of membranes 44 which retain a plurality of beads or particles 42. The beads or particles may be made from a wide variety of different materials including glass, silica gel, platinum, polyester, polyamide or nylon.

The disc 42 is advantageous in certain applications. For example, when a colloidal suspension is inserted into the filter 40, the liquid portion of the colloidal suspension is able to pass through the disc 42 but the disc may provide a barrier against the passage of the colloid.

The filters 30 and 40 have the same mechanical advantages as the filter 10 in the embodiment shown in FIGS. 1, 2 and 3. For example, the discs in these filters are rigidly supported on their associated support members and are capable of withstanding forces as high as ten thousand times gravity (10,000 g) in a centrifuge. Furthermore, fluid is able to flow only through the discs, even at these high forces, without leaking through the support members or through the areas common to the discs and the support members. As will be appreciated, the term "disc" as applied to the members 30 and 40 is used generically in the same sense as the term "disc" when applied to the member 10.

Although the retainers (such as the retainers 36 and 38) for the filters 30 and 40 are preferably made from a material such as Teflon, other materials may be used. However, it is desirable for the filaments in such material to have a diameter in the order of ten (10) to five hundred (500) micrometers ($\mu$m). It is also desirable that the melting temperature of the material in the retainers be approximately 10° C. higher than the melting temperature of the material such as polypropylene in the supporting member such as the member 32. For example, the retainers can be made from carbon fibers, polyamide fibers, glass fibers, ceramic fibers or metal fibers such as platinum.

As another example of a combination of a support member (such as the member 32) and a retainer (such as the retainer 36), the support member may be made from a glass having a wall thickness in the order of one half millimeter (0.5 mm) to two millimeters (2 mm). The support member may be melted into a retainer of glass fibers having filaments with a thickness in the order of three (3) to one hundred (100) micrometers ($\mu$m). Specific examples are a support member made from flint glass and a retainer of a borosilicate or a fused silica. Another specific example is a support member made from a borosilicate and a retainer made from a fused silica.

The filters shown in FIGS. 1 through 7 and described above may be inserted in a tray generally indicated at 60 in FIGS. 8 and 9. The tray 60 may be made from a suitable material such as glass, polypropylene, polyamide, Teflon, other plastics, metal, ceramic, or a composite of the preceding materials. The particular material selected for the tray 60 is dependent upon the application and the requirement for, or the desirability of, chemical inertness. The tray 60 may be formed from a flat member 61 embodying conical protrusions 62 integral with the tray. The protrusions 62 can be provided with discs 68 to function as the filters 10, 30 and 40. These filters are generally indicated at 66. The protrusions are open at their opposite ends to provide for a flow of fluid through the discs. Instead of forming the filters 66 integrally with the tray 60, the filters may be formed separately and may then be inserted into receptacles corresponding to the protrusions in the tray.

The provision of filters 66 into a tray such as the tray 60 is desirable because it facilitates a simultaneous and substantially uniform operation on a plurality of filters. To facilitate a centrifugal operation on the filters in the tray 64, the tray 64 may be inserted into a holder generally indicated at 70 in FIG. 10. The holder 70 has a plurality of tubes 72 for receiving the filter ends 63 in the tray 64. The tubes 72 in the holder 70 may be elongated to provide for an orderly flow of fluid from the tubes when the tray 64 and the holder 70 are centrifuged. The tray 64 is in a compatible relationship with holders for a Microfuge B. Similarly, a centrifugal operation on the filters in the tray 60 can be accomplished with a properly adapted centrifuge head. For example, a set of ninety six (96) filters in a tray can be simultaneously processed by filling, washing, extracting or emptying the filters within a period of approximately one (1) minute.

FIG. 11 illustrates an arrangement for introducing a vapor into a plurality of filters. This arrangement includes a container 80 having a cap 82. An absorbent sheet 84 made from a suitable material such as paper or glass fibers may be disposed in the container 80 against the inner wall of the container. For example, the absorbent sheet 84 may be made from a Whatman GF/C material. The filter paper 84 may be maintained against the side wall of the container 80 as by a Teflon screen 86 with mesh openings which may be of four thousandths of an inch (0.004"). When moistened with the same fluid 96 as in a flask 94, this moistened absorbent sheet maximizes the vapor content within the container.

A centering member 88 is disposed at the bottom of the container 80. The centering member 88 may preferably have a conical configuration. The centering member 88 is constructed to support the tray 60 shown in FIG. 8 and described above so that the tray and the filters in the tray do not contact the wall of the container 80 or the filter paper 84. In this way, an efficient transfer of vapor can be provided between the container and the filters in the tray.

A conduit 90 extends from the interior of the container 80 through the cap 82 and through a cap 92 to the vapor flask 94. The conduit 90 may be made from a suitable material such as a tetrafluoroethylene (Teflon). The liquid 96 to be vaporized is disposed in the flask 94. The vapor from this liquid passes through the conduit 90 into the container 80 for filling the filters in the container.

The cap 92 has an inlet 98 for receiving nitrogen. The nitrogen may be introduced into the flask 92 through an inlet 98 to flush the container 80 with an inert gas. In this way, the container 80 may be flushed of reactants after use in one reaction and prepared for use in a subsequent reaction.

These filters are optimally suited for use in manual peptide sequencing by Edman degradation, manual peptide synthesis, and in other analytic or diagnostic processes requiring rapid transfer of reagents by capillary action, solvent rinsing by centrifugation or permeation by gas phase reagents or solvents.

Use of filters in peptide sequencing

In the case of manual Edman chemistry, a process used to remove sequentially one amino acid at a time from polypeptides starting at the $NH_2$-terminal end, the filters and trays of this invention provide for a user to achieve both liquid and gas phase reactions rapidly, together with solvent rinses and drying steps, more conveniently than has been possible in the prior art.

The articles and apparatus described above have been used in manual Edman chemistry to sequence a peptide. The filters have been constructed as shown at 10 in FIGS. 1, 2 and 3 and have included the disc 18 with a diameter of one and two tenths millimeters (1.2 mm) and a weight of approximately seventy five micrograms (75 $\mu g$). The filter discs 18 have been prepared from a glass fiber filter sheet (Whatman GF/C) which has been derivatized with trimethylsilyl groups. The filter discs 18 have been inserted into the support members 12, which have been provided with a diameter of approximately one millimeter (1.0 mm) at the end 16. These support members are cut from Eppendorf pipet tips designated as part no. 5089-801 and provided by American Scientific Products. Each of the filters 10 has been provided with a length of approximately six and one half millimeters (6.5 mm).

A set of eight (8) filters 10 has been inserted into the trays 64. The trays 64 have been provided with dimensions of approximately fifty millimeters (50 mm) by twelve millimeters (12 mm) by one millimeter (1 mm) or one and one half millimeters (1.5 mm). The array of filters in the tray 64 was complementary to a Microfuge B centrifuge tube holder such as shown at 70 in FIG. 10.

A disc 18 in a filter such as 10 (FIG. 1) has been prewetted with a ten percent (10%) solution of Polybrene in water (Aldrich part no. 10768-91) and dried under nitrogen for several minutes. The amount used of this Polybrene solution has been in the order of one half microliter (0.5 $\mu l$ to one microliter 1.0 $\mu l$). Polybrene is desirable because it has a high affinity for peptides and proteins. A polypeptide sample (in the ng to $\mu g$ range) in a volume in the order of one half microliter (0.5 $\mu l$) to one microliter (1.0 $\mu l$) has then been drawn into the disc 18 by capillary action or by centrifugation through the filter.

The disc 18 has then been wetted by a capillary action with a reagent constituting five percent (5%) by volume of phenylisothiocyanate in heptane. A tray 64 as shown in FIG. 10 for holding the filter 10 has then been placed in a container, such as the container 80, containing a saturated atmosphere of triethylamine in water. The time of the reaction has been approximately ten (10) to fifteen (15) minutes and the temperature of the reaction has been approximately 50° C. Thereafter, the filter in the tray 64 has been dried by vacuum for a period of approximately three (3) minutes, rirsed three (3) times with ethyl acetate by dipping (15 $\mu l$ per capillary) and three (3) times centrifuged at ten thousand revolutions per minute (10,000 rpm/min.).

The tray 64 with the filter 10 has then been transferred to a second container 80 saturated with a vapor of anhydrous trifluoracetic acid. The time of the reaction has been approximately ten (10) to fifteen (15) minutes and the temperature of the reaction has been approximately 50° C.

The filter 10 held by tray 64 has then been assembled with a holder 70 of FIG. 10. The holder 70 has been provided with a polypropylene microtube (Cole Scientific, Calabasus, Calif.) with a volume of three hundred microliters (300 $\mu l$) and centrifugally rinsed at approximately ten thousand times gravity (10,000 g) with approximately fifteen microliter (15 $\mu l$) of butyl chloride per filter. The butyl chloride rinse containing the anilinothiazolinone derivative of the amino acid cleaved from the polypeptide has been dried in a vacuum centrifuge. The residue has been treated with approximately ten microliter (10 $\mu l$) of twenty five percent (25%) aqueous trifuoroacetic acid for approximately fifteen (15) minutes at 50° C. for conversion to the phenylthiohydantoin derivative. This derivative has been identified by reverse phase high performance liquid chromatography (HPLC).

The steps discussed above have been repeated in sequence to separate the second amino acid from the $NH_2$-terminus of the polypeptide (less the first amino acid). Subsequent cycles as specified above cause the successive amino acids to be cleaved from the $NH_2$-terminus of the polypeptide (less the previously cleaved amino acids). The cleaved amino acids phenylthiohydantoins have been identified by HPLC.

The filters 30 shown in FIGS. 4 and 5 and described above have also been used to sequence peptides by the use of Edman chemistry. In this use, the filters 30 have been provided with a capacity of approximately three hundred microliter (300 $\mu l$). The filters have been provided with an inner diameter of approximately four millimeters (4 mm) at the opening corresponding to the opening 16 and an outer diameter of approximately five millimeter (5 mm) at this opening. At the opening corresponding to the opening 14, the filter 30 has been provided with an inner diameter of approximately six millimeters (6 mm) and an outer diameter of approximately seven millimeters (7 mm). The overall length of the filter has been approximately thirteen and one half millimeters (13.5 mm). A cone of approximately 13° has been maintained to a length of approximately nine millimeters (9 mm).

The disc 34 in the filter 30 has been spotted with approximately four microliter (4 $\mu l$) of a one hundred microgram per microliter (100 $\mu g/\mu l$) solution of Polybrene and dried under nitrogen. The steps involving Edman chemistry have been performed as specified above. However, the solvents ethyl acetate and butyl chloride have been applied with a micropipet rather than by capillary action, and the capacity of the container corresponding to the container 80 has been approximately twenty five milliliter (25 ml).

The above examples represent the sequencing of a single peptide. Multiple peptides can be similarly sequenced utilizing multiple filters as depicted in FIGS. 8–11.

Use of filters in peptide synthesis

The discs 18 have been one and two tenths millimeter (1.2 mm) in diameter and approximately seventy five micrograms (75 $\mu g$) in weight. For peptide syntheses, the discs have been prepared from aminopropylsilylated glass fiber sheet (Whatman GF/C).

The filters of this invention provide for a unique approach for the use of peptides attached to glass supports or, in connection with the use of the embodiments of the filter shown in FIGS. 6 and 7, a comparable synthesis on aminated polystyrene supports.

To accomplish the aminopropylsilylation, the discs have been immersed in a reagent containing one (1) part by volume aminopropyltriethoxysilane, one (1) part by volume of pyridine and eight (8) parts by volume of tetrahydrofuran. This immersion has occurred for approximately thirty (30) minutes in the absence of moisture, for approximately ten (10) to fifteen (15) minutes in the presence of moisture (air saturated with moisture vapor) and for an additional sixty (60) minutes in the absence of moisture. The derivatized discs have thereafter been successively washed with tetrahydrofuran, methanol and tetrahydrofuran and then air dried. Actually, any procedure capable of introducing a reactive amino group can be used for peptide synthesis.

The sequence of steps for synthesizing the peptides and the materials used for synthesizing the peptides have been the same as employed in the prior art to obtain the attachment of an acid or base cleavable linkage to the amino group of the support, followed by sequential addition of appropriately blocked α-NH$_2$ amino acids through their carboxyl groups. However, multiple samples have been handled simultaneously in this invention and transfers of reagents have been made by capillary action.

The steps described above may be repeated any desired number of times to produce a peptide of any desired length. This process can be used to produce multiple copies of a single peptide. The process can also pe used to produce single copies of multiple peptides using multiple filters as depicted in FIG. 10.

The peptides synthesized as described above may be removed from the solid phase and purified or, if desired, left on the solid phase for direct use in immunoassays. In this case, it is useful to employ eirher a strategy of synthesis wherein a peptide can be deblocked without removal from the solid phase support or is attached directly to a non-cleavable functional group on the support Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. Apparatus for receiving a substance and for changing the characteristics of the substance comprising: means enabling substantially complete comingling of minute volumes of reactants for chemical reaction and substantially complete recovery of the reaction products therefrom, including
    a hollow conical support member made of fluid-tight plastic material and having a large end and a smaller end, the large end being open, the smaller end having a front edge; and
    a disc of hard, fibrous material being plugged from the larger end into the smaller end of the support member, said disc being seated under radial compression inside the support member substantially flush with the front edge of the smaller end of the support member, the hard fibrous material of the disc cooperating with the plastic material of the support member to retain the disc in fixed relationship to the support member so as to withstand centrifugal forces when being centrifuged.

2. Apparatus as set forth in claim 1, the disc being in a fused relationship with the support member.

3. Apparatus as set forth in claim 2, including at least one retainer of mesh material being welded to the support member retaining the disc in fixed relationship to the support member.

4. Apparatus as set forth in claim 3, including a second retainer of mesh material being welded to the support member spaced from the first retainer, the disc being disposed between the first and second retainer.

5. The apparatus of claim 1, wherein the apparatus is used for fluids and wherein the fixed relationship between support member and disc prevents leakage of fluid at the seam between the disc and support member.

6. Apparatus for processing a fluid comprising: means enabling substantially complete comingling of minute volumes of reactants for chemical reaction and substantially complete recovery of the reaction products therefrom, including,
    a plurality of hollow conical support members are made from fluid-tight plastic material each having a large end and a smaller end, the large end of each support member being open, the smaller end of each support member having a front edge;
    a plurality of discs each of hard, fibrous material, each disc being plugged from the larger end of each support member into the smaller end, each disc being seated under radial compression inside each support member substantially flush with the front edge of each smaller end of each support member;
    each support member having a dimension at its larger end to provide for liquid uptake by capillary action;
    the fibrous material of each disc cooperating with the plastic material of each support member to retain each disc in fixed relationship to each support member so as to withstand centrifugal forces when being centrifuged; and
    a support tray receiving a plurality of the support members and disc for the flow of fluid through the support members and the discs when the support tray is centrifuged.

7. Apparatus as set forth in claim 6, including:
    a pluarlity of retainers each made from a mesh material and welded to an associated one of the support members; and
    each of the retainers being disposed relative to an associated one of the discs to support the associated discs in rigid relationship to the associated support member.

8. Apparatus as set forth in claim 6, wherein the fibers in each of the discs have a thickness in the order of 50 micrometers to 5.0 micrometers.

9. Apparatus for operation on a fluid, comprising: means enabling substantially complete comingling of minute volumes of reactants for chemical reaction and substantially complete recovery of the reaction products therefrom, including,
    a hollow container defined by at least one wall;
    a sheet made from a fibrous material disposed against the wall of the container to become wetted by fluid introduced into the container;
    means for holding the fibrous sheet against the wall of the container;

a tray;

a plurality of support members disposed in the tray and made from a nonporous material, each of the support members being open at first and second opposite ends;

a plurality of discs made from a porous material and each plugging the second end of the associated one of the support members in a leak-proof relationship at the seam between the support member and the associated disc; and centering means disposed in the container for positioning the tray in the container to avoid contact between the sheet of the fibrous material and the support members and disc disposed in the tray; and means disposed in cooperative relationship with the container for introducing a vaporized fluid into the container for an operation on the fluid by reaction of materials within the container during the passage of fluid through the discs.

10. Apparatus as set forth in claim 9, the holding means including a screen and the centering means including a cone disposed in the container for receiving the tray, 11. Apparatus for enabling microvolumes of fluids to co-react, comprising: means enabling substantially complete comingling of minute volumes of reactants for chemical reaction and substantially complete recovery of the reaction products therefrom, including, a hollow, conical support member made of fluid-tight plastic material and having a first end opening and a second end opening, said first end opening being larger than the second end opening, said second end also having a front edge;

a disc of hard, fibrous, porous material having an upper and lower surface and having been force fit into the second end opening through the first end opening so as to be seated under radial compression inside the support member, the lower surface of said disc being flush with the front edge of said second end; and said hard, fibrous material of the disc cooperating with the plastic material of the support member to retain the disc in fixed relationship to the support member so as to withstand centrifugal forces when being centrifuged.

12. The apparatus of claim 11, wherein the disc and support member are dimensioned so that they are capable of retaining fluids by capillary action.

* * * * *